United States Patent
Yin et al.

(10) Patent No.: US 6,386,050 B1
(45) Date of Patent: May 14, 2002

(54) NON-INVASIVE FLUID FLOW SENSING BASED ON INJECTED HEAT TRACERS AND INDIRECT TEMPERATURE MONITORING

(75) Inventors: Hongfeng Yin, San Jose; Catherine Templin, Portola Valley, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/468,695

(22) Filed: Dec. 21, 1999

(51) Int. Cl.$^7$ .............................. G01F 1/708; G01F 1/68
(52) U.S. Cl. ................. 73/861.95; 73/861.07; 73/204.14
(58) Field of Search .................. 73/861.95, 861.07, 73/204.14

(56) References Cited

U.S. PATENT DOCUMENTS

| | | | | |
|---|---|---|---|---|
| 3,807,228 A | * | 4/1974 | Matzuk | 73/861.95 |
| 4,458,709 A | * | 7/1984 | Springer | 73/861.95 |
| 4,480,483 A | * | 11/1984 | McShane | 73/861.95 |
| 4,938,079 A | | 7/1990 | Goldberg | 73/861.95 |
| 5,260,665 A | * | 11/1993 | Goldberg et al. | 73/861.95 |
| 5,325,170 A | | 6/1994 | Bornhop | 356/128 |
| 5,623,097 A | | 4/1997 | Horiguchi et al. | 73/204.15 |
| 5,726,357 A | | 3/1998 | Manaka | 73/204.26 |
| 5,763,775 A | | 6/1998 | Sato et al. | 73/204.26 |
| 5,764,539 A | | 6/1998 | Rani | 364/557 |

OTHER PUBLICATIONS

Gas, B., et al., "High–Frequency Contactless Conductivity Detection in Isotachophoresis," Journal of Chromatography, 192 (1980), pp. 253–257.

Lammerink, Theo S.J., et al., "Integrated Micro–Liquid Dosing System," IEEE 0–7803–0957–2/93 (1993), pp. 254–259.

Tarigan, Hendra J., et al., "Capillary–Scale Refractive Index Detection by Interferometric Backscatter" Analytical Chemistry, vol. 68, No. 10 (1996), pp. 1762–1770, May 1996.

* cited by examiner

Primary Examiner—Harshad Patel (57) ABSTRACT

A system and method for measuring flow rate within a fluid-bearing passageway include introducing heat fluctuations into the flow and then non-invasively monitoring the effects of the heat fluctuations propagating to or from one or more interrogation regions. In one embodiment, the non-invasive monitoring detects fluctuations in the refractive index of the flowing fluid as a result of variations in the temperature of the fluid. In another embodiment, electrical conductivity of the fluid is monitored. The heat fluctuations may be introduced using an optical heat generator, such as an infrared laser, or may be introduced using an electrical member, such as a heater coil. Determining the refractive index along the interrogation region may be achieved by monitoring characteristics on an interference pattern, but other optical arrangements may be utilized.

19 Claims, 9 Drawing Sheets

NON-INVASIVE FLUID FLOW SENSING BASED ON INJECTED HEAT TRACERS AND INDIRECT TEMPERATURE MONITORING

TECHNICAL FIELD

The invention relates generally to systems and methods for measuring low volume flows of liquid and relates more particularly to non-invasively measuring flow rates within liquid analysis systems and drug delivery systems that require a high degree of flow measurement accuracy in extremely low volume applications.

BACKGROUND ART

Accurate measurements of low volumetric liquid flow rates are important in many analytical applications, such as flow injection analysis, micro-bore liquid chromatography, capillary chromatography, capillary electrophoresis, and bioassay applications. Precise measurements are also important in drug delivery applications. The flow rate in analytical systems may be in the range of 0.0001 milliliter/minute (ml/min) to 1 ml/min. In medical applications, the flow rate may be as low as 0.008 ml/min for ambulatory infusion. In addition to accuracy, other concerns in selecting an approach for measuring flow rate include providing a fast dynamic response and minimizing the risk of introducing contamination into the flow of liquid.

The most common approaches to measuring flow rate incorporate a heater and at least one temperature-sensitive resistor within the flow channel. In a thermal transit-time approach, the heater is supplied with a signal, such as a square-wave voltage at a selected frequency, to inject heat pulses as tracers into the fluid of interest. The periodic heat tracers travel along the flow channel, causing periodic temperature fluctuations downstream. The heat tracers are detected by a thermistor or other temperature sensing device that is located within the flow. In steady state, the phase shift of the downstream thermal fluctuations relative to the upstream thermal fluctuations are related to the mean velocity of the fluid. This approach has little dependency on the ambient temperature and on the properties of the liquid, so that the transit time can be determined accurately.

In a thermal dilution flow approach, three resistors may be located along a flow channel, with the center resistor being used as the heater and the end resistors being used as temperature-sensitive members. Current is passed through the heater to trigger a change in temperature within the liquid flow. The two temperature-sensitive resistors are located equidistantly from the heater resistor and are used to sense the heat distribution from the center. Flow rate is determined as a function of the temperature difference between the upstream and downstream temperature-sensitive resistors.

One approach that does not utilize temperature-sensitive members is the differential pressure flow approach. In laminar flow conditions with low Reynolds numbers, the pressure difference across an orifice is proportional to the flow rate.

There are a number of concerns with these conventional approaches to determining flow rate. A first concern is that contact with the flowing liquid will introduce contamination into the stream. A contamination-free approach to determining flow rate is important in chemical analysis applications and drug delivery applications. Another concern is that the approaches may not be sufficiently sensitive at extremely low flow rates.

Systems for measuring liquid flow rates without contacting the liquid are described in U.S. Pat. No. 5,764,539 to Rani and U.S. Pat. No. 4,938,079 to Goldberg. In Rani, a pump is operated to deliver a fluid in pulses. The fluid flows through a fluid delivery tube. A sensor is in contact with the outer surface of the fluid delivery tube in order to detect the temperature of the outer surface. The sensor is calibrated at an initial temperature and is responsive to the flow of fluid through the tube. Since fluid flow will increase the temperature at the outer surface of the tube, the output of the temperature-sensitive sensor is indicative of the flow rate through the tube. While the Rani system may operate as designed, the sensitivity of the measurements may not be sufficient at the flow rates associated with many analytical systems and medical applications. Moreover, the pulsed deliveries may not be desirable in many applications.

The Goldberg system utilizes microwave energy to determine flow rates. A thermal marker is introduced into the flow of liquid to be measured. For example, a heat pulse may be generated by radiating energy into the stream using a microwave heating device. An alternative means of introducing the thermal marker is through the use of focused infrared energy produced by a laser or other source. The flow rate may be measured by determining the transit time of the thermal marker from the heater to a sensor. In the preferred embodiment, the liquid conduit is passed through a resonant microwave cavity such that the resonant characteristics of the cavity are affected by the passage of the thermal marker. For example, the dielectric constant of the liquid will change with temperature, so that the resonant frequency of the microwave cavity will vary with passage of the thermal marker through the cavity. The Goldberg system is designed to provide accuracy at flow rates below 100 cc/hour. However, the use of microwave signals limits the sensitivity of the system. As a consequence, the Goldberg system is not easily adapted to use in micro fabricated devices and micro analysis systems.

U.S. Pat. No. 5,726,357 to Manaka and U.S. Pat. No. 5,623,097 to Horiguchi et al. describe micro fabricated devices which employ the thermal approaches described above. Thus, the flow sensors are highly sensitive, but directly contact the flowing fluid. In Manaka, a substrate is patterned to include a heating portion and a sensing portion. The transit time for heat transfer from the heating portion to the sensing portion is used to calculate flow rate. Similarly, the Horiguchi et al. sensor includes a substrate through which a fluid path is formed. A bridge is suspended over the fluid path. A heating resistor and a temperature sensor are formed on the bridge through an interlayer isolating film that is designed to eliminate the difference between the temperature of the heater and the heat sensor. A temperature compensating circuit may be used to offset any remaining effects of thermal communication between the heater and the temperature sensor.

While known approaches operate as designed, what is needed is a system and a method for monitoring fluid flow in a manner that does not introduced contamination into the flow and that is easily adapted to applications having a small cell volume.

SUMMARY OF THE INVENTION

A system for measuring flow rate within a fluid-bearing passageway includes introducing a heat tracer into the flow and includes non-invasively and indirectly monitoring the effects of the heat tracer as it propagates to one or more interrogation regions. Typically, the heat tracer is one thermal fluctuation introduced by a modulating heat generator. In one embodiment, the non-invasive monitoring occurs optically. In another embodiment, the electrical conductivity of the fluid is monitored. Based upon the detection of changes in the physical properties of the fluid that propagates through interrogation regions, the rate of flow of the fluid is identified. For example, the phase shift between the modulations of the heat generator and the modulations of temperature-dependent physical properties (optical or electrical) may be used to determine flow rate.

In any of the embodiments, the heat tracer may be introduced using an optical heat generator. For example, the heat generator may include an infrared laser, infrared lamp or a light emitting diode (LED) that generates a beam that is incident to the flow of fluid through a capillary or a micro channel of a micro analytical device. In an alternative embodiment, the heat generator is a coil that is in thermal communication with the passageway, but is removed from direct contact with the fluid.

At least one temperature-dependent property of the fluid is measured upstream of the heat generator, downstream of the heat generator, or both. Thus, the temperature of the fluid is not detected directly. For the optical sensing embodiment, the effects of fluctuations in the refractive index of the fluid sensed. For example, the system can monitor changes in a back-scattered or forward-scattered interference pattern generated as a result of light interacting with the fluid and the structure of the passageway. On the other hand, the electrical sensing embodiment forms a capacitive cell for monitoring resistivity.

In the optical sensing embodiment, the detector includes an optical arrangement having a light source which is spatially removed from the fluid-bearing passageway, while being optically coupled to the passageway at the interrogation region. Typically, the interrogation region is downstream of the heat generator, but the interrogation region may be coincident with the heating region, so that heat tracers are monitored as temperature fluctuations within the interrogation region in which they are introduced. As another alternative, a second interrogation region may be included upstream of the heat generator, particularly if a thermal dilution flow approach is utilized. Regardless of the position of an interrogation region, if the heat tracers are introduced in a repeating pattern (e.g., sine wave pattern), the modulations of the temperature-dependent physical properties of the fluid are used to determine flow rate.

At each interrogation region, a detector is positioned to receive light energy originating from the associated light source and redirected at the interrogation region as a result of interaction with the passageway and with the fluid in the passageway. The detector has an output that is responsive to the reception of light energy. In one application, the detector is positioned to detect an interference pattern generated by light interacting with the fluid and light interacting with the passageway. As is well known in the art, the back-scattered interference pattern may be formed as a consequence of constructive and destructive interference when light is reflected at both the "forward" fluid-to-passageway interface and the "rearward" fluid-to-passageway interface. The phase difference between the two reflections determines the characteristics of the interference pattern. Since the phase shift will vary with changes in the refractive index of the fluid and since the refractive index will vary with changes in temperature of the fluid, the interference pattern is responsive to the temperature of the fluid. A similar interference pattern is generated by the forward-scattered light and may alternatively be used.

The detector may have a field of view that is sufficiently large to detect a number of minima and maxima of the interference pattern. Alternatively, the detector may be an optical fiber or other single element sensing arrangement having an aperture with a size that is insufficient to detect adjacent minima or adjacent maxima in the intensity modulated profile of the interference pattern. The single-element sensing arrangement provides a less expensive and less complex detector than would be necessary if multiple minima and maxima were imaged.

As an alternative to detecting the interference pattern, the optical embodiment may be implemented by placing the detector to sense light energy that propagates through the fluid. The angle of the axis of the exiting beam is dependent upon the refractive index of the fluid. Consequently, the position of the exit beam can be used to determine when a heat tracer passes the interrogation region.

In the optical embodiments, the interrogating light source that is directed into the fluid is preferably a "non-thermal beam." A non-thermal beam will be defined herein as one that experiences a low absorbency during propagation through the fluid. A beam having a center frequency below 1100 nm (i.e., at or below the near infrared) is typically non-thermal.

In the second embodiment of the invention, the resistivity of the fluid within the passageway is monitored to detect when a heat tracer propagates through an interrogation region. In the same manner as the optical embodiments, the time required for passage of a heat tracer from the heat generator to the interrogation region is used to calculate flow rate. For a repeating pattern of heat tracers, the phase difference between the introduction of the heat tracers (i.e., thermal fluctuations) and resistivity fluctuations may be utilized. Resistivity (and therefore conductivity) of the fluid may be monitored by placing electrodes adjacent to the outside wall of the passageway and supplying a high frequency signal to the electrodes, thereby forming a capacitive cell. For almost all liquids having a non-zero level of conductivity at a particular temperature, the resistivity will decrease with increases in temperature. As a result, monitoring the resistivity provides a reliable means for detecting the time at which a heat tracer reaches the interrogation region of the passageway.

While not critical, the system and method are easily adapted to use with micro fabricated devices. The heaters and optical components may be coupled to the same substrate as micro machined valving components. Consequently, the system may be integrated into a micro analysis system or a micro-drug delivery and dosing system. The fluid-bearing passageway may be a capillary used in capillary chromatography or capillary electrophoresis. Flow rates as low as 0.0001 ml/min may be accurately measured.

One advantage of the invention is that the system and method may be used in applications having extremely small cell volumes, such as those used in micro analytical devices, since there is no need for making contact between a probe and the liquid of interest. Another advantage is that the system does not introduce contamination into the fluid, since direct contact is avoided. Yet another advantage is that substrate temperature does not need to be measured, because the substrate temperature does not contribute to the measurement of flow rate. In many known uses of thermal sensors to monitor temperature directly, the substrate temperature is a factor and temperature compensation is used to offset the effects of thermal radiation from the heater to the sensor. By utilizing a method that does not directly measure temperature, any direct radiation from the heater to the sensor of the present invention does not affect the calculation of flow rate. Furthermore, there is no heat loss from the fluid to the detector, as there would be if the system required the detector to be thermo-coupled to the fluid. Additionally, the method is more readily adaptable for use in micro flow applications, as compared to methods that utilize temperature sensors to detect heat tracers. There are difficulties associated with fabricating and coupling heat sensors that are sufficiently small and sufficiently sensitive for micro flow applications.

Optionally, the system may be used to control the liquid temperature within the fluid-bearing passageway. The measurement of temperature-dependent physical properties of the liquid flow may be used to monitor liquid temperature and to provide a feedback control of the heater.

As other options, the interrogation region may be coincident with the region in which the heat tracers are introduced (as noted above) or a non-thermal tracer can be substituted for the heat tracer. For example, the composition of the fluid, which also affects the refractive index, may be intentionally fluctuated to provide a non-thermal means for determining flow rate.

DETAILED DESCRIPTION

Figure 1:
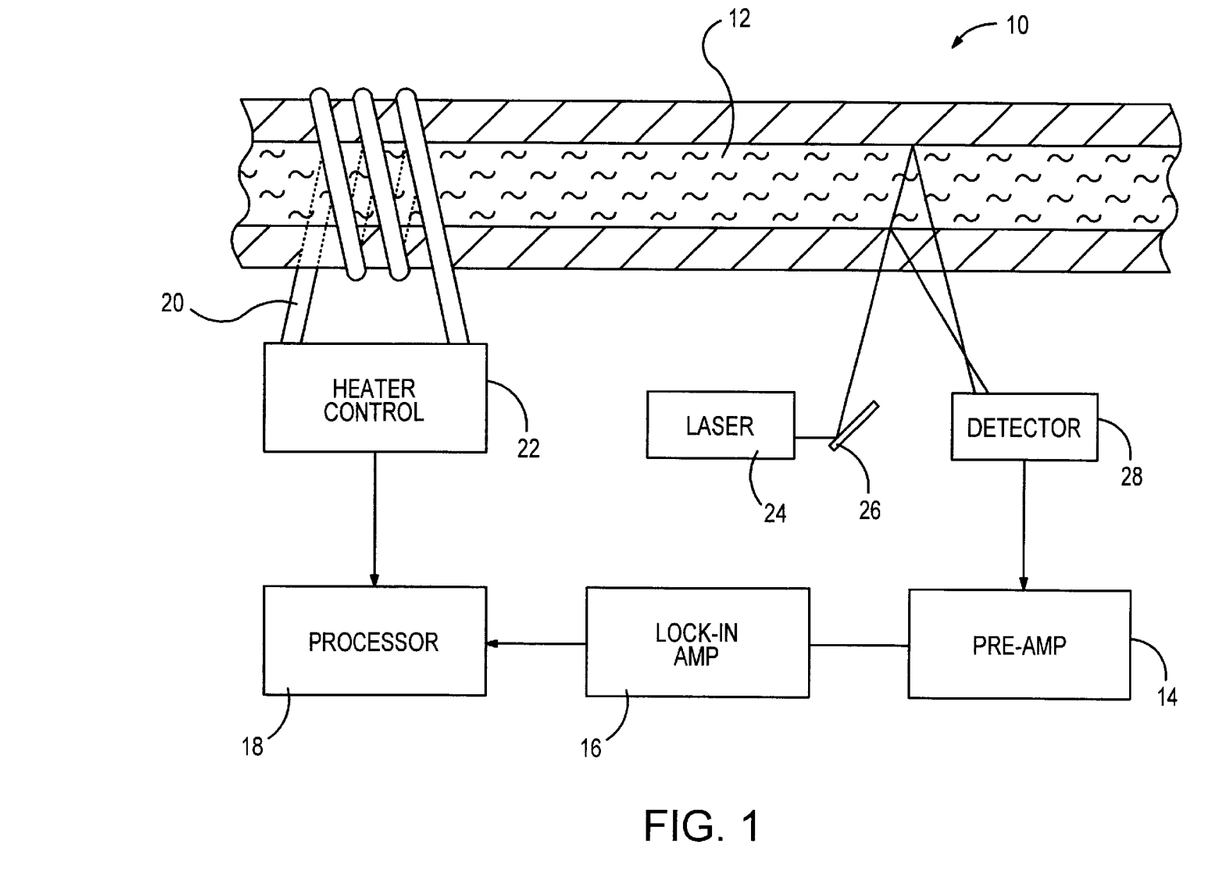
FIG. 1 is a schematic view of a non-invasive fluid flow sensing system in accordance with one embodiment of the invention.

With reference to FIG. 1, a first embodiment of a non-invasive system 10 for determining flow rate within a fluid-bearing passageway 12 monitors the refractive index of the fluid within the passageway in order to obtain data for calculating flow rate. The system may be a micro analytical system, such as the type used in chemical analysis or medical analysis applications. Optionally, many of the components of the system are fabricated on a single substrate, such as a silicon chip. For example, a preamplifier 14, a lock-in amplifier 16 and a processor 18 may be formed on a silicon substrate. The passageway 12 may be a channel that is etched into the substrate or may be a capillary tube that is fixed to the substrate. Integrated circuit fabrication techniques are well known in the art. Additionally, some of the components may be off-chip, particularly the processor 18.

The component arrangement of FIG. 1 is merely exemplary. That is, other components may be utilized, as will be explained more fully below. The system 10 includes a heater 20 and a heater control device 22. The heater control device may energize the heater in a fixed repeating pattern (e.g., a sine wave pattern). A laser 24 introduces an interrogation beam, which is reflected at the "forward" and "rearward" interfaces of the fluid with the wall of the passageway 12. A detector 28 senses an interference pattern which is dependent upon the temperature of the fluid within the passageway. The output of the detector is amplified by the preamplifier 14. The lock-in amplifier 16 cooperates with the processor 18 to monitor the phase difference between the fixed repeating pattern defined by the heater control device 22 and the changes in the interference pattern, as sensed by the detector. In one embodiment, the phase difference is used to identify the flow rate of the fluid.

In analytical applications, the passageway 12 may be a capillary having a cross sectional dimension (e.g., an inside diameter for a circular capillary or a side for a rectangular capillary) in the range of 5 $\mu$m to 500 $\mu$m. The flow rate within capillary electrophoresis may be as low as 0.0001 ml/min. A capillary typically includes a coating, such as a polyimide coating. The coating is not shown in FIG. 1. A portion of the coating may be removed in order to form a window to allow increased penetration of light into the passageway, but coating removal is not critical.

The flow rate sensing system 10 includes a heater 20. In the micro fabricated embodiment, the heater is a serpentine pattern of traces through which current is conducted in order to generate heat in the area of the passageway 12. Micro fabricated heaters are well known in the art. As previously noted, the operation of the heater is controlled by the heater control device 22. The heater is activated in a known pattern in order to introduce heat tracers into the flowing fluid within the passageway 12. For example, sine wave or square wave activation may be employed. In the embodiment of FIG. 1, the transit time for passage of a heat tracer from the region of the heater to an interrogation region is determined in order to identify the flow rate. However, the heater may be located within the interrogation region. As will be described more fully below, the thermal dilution approach may also be used.

The thermal energy that is introduced to the fluid by the heater 20 should be sufficiently great that the change in temperature of the fluid is perceivable using the techniques to be described below. However, the increase in temperature should not affect the chemical composition of the fluid. Optionally, the system may include a feedback loop to the heater controller 22 to provide active temperature control. When chemical reactions, such as polymer chain reactions, are carried out in the micro fabricated flow cell, it is essential to monitor and control the liquid temperature. The feedback control of the heater 20 can be achieved using the indirect temperature measurement techniques that will be described.

Figure 2:
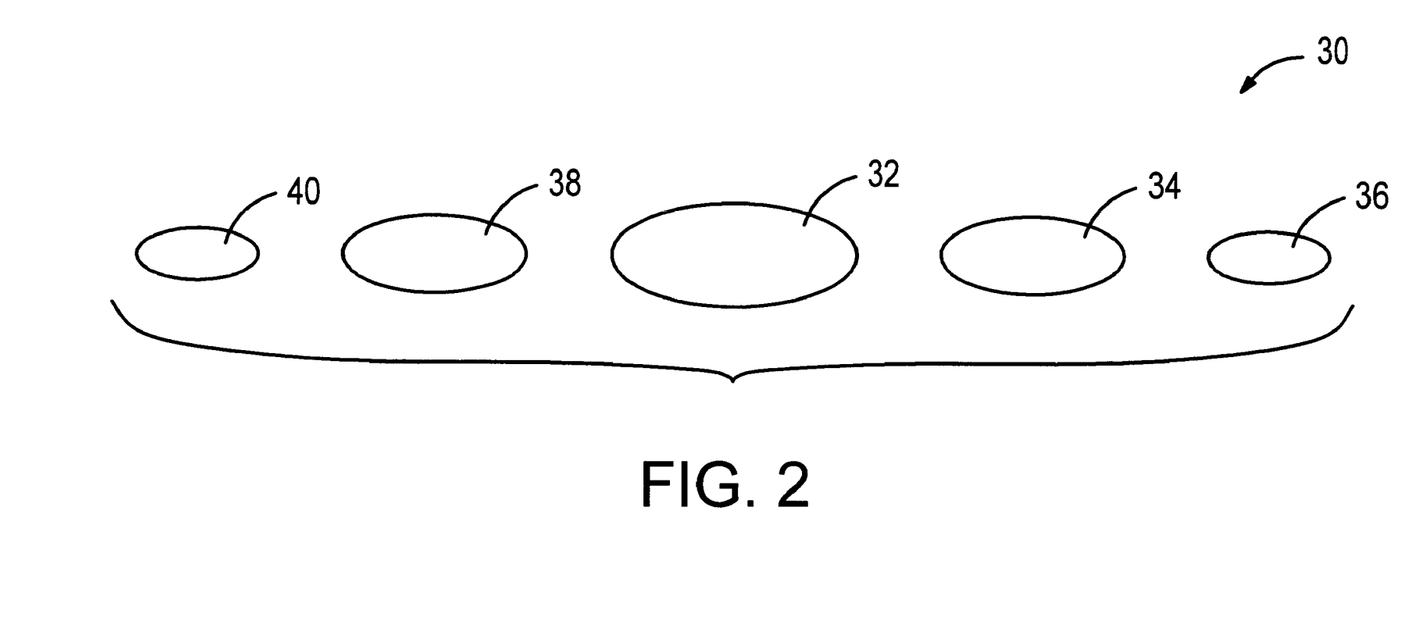
FIG. 2 is a representation of an interference pattern that is generated at the detector in the system of FIG. 1.

The system 10 includes the laser 24. Preferably, the laser is a "non-thermal" laser, i.e., one that generates light at a frequency which is not readily absorbed by the flow of fluid. For example, the laser may be a diode laser having a center frequency that is below 1100 nm. A helium-neon laser beam may be reflected by the mirror 26 toward a window within the fluid-filled passageway 12. One portion of the beam will be reflected at the "forward" interface of the fluid and the wall of the passageway. A second portion will be reflected at the "rearward" interface of the fluid and the passageway. As a result of constructive and destructive interference, a forward-scattered or back-scattered interference pattern will be generated and monitored by the detector 28. As is known in the art, the interference pattern is a series of maxima and minima in an intensity modulated beam profile that emerges radially from the passageway. Interference patterns are currently used in the industry and are described in an article entitled "Capillary-Scale Refractive Index Detection by Interferometric Backscatter" (*Analytical Chemistry*, Vol. 68, No. 10, May 15, 1996, pages 1762–1770), by H. J. Tarigan et al. A typical interference pattern is graphically represented in FIG. 2, where the pattern is perpendicular to the capillary axis. The pattern includes a center large maximum 32 and progressively smaller maxima 34, 36, 38 and 40. The minima (i.e., nulls) are located between the maxima.

Typically, the beam of laser light is introduced at a non-right angle to the axis of the fluid-bearing passageway 12. In the embodiment of FIG. 1, the detector is a multi-element device, such as a charge coupled device (CCD). When light enters the fluid at the forward fluid-to-passageway interface, the light will be redirected, since there is a refractive index mismatch between the fluid and the structure that forms the passageway. The refractive index of the fluid will change with changes in the temperature of the fluid. As a result, the interference pattern will shift in position with changes in temperature. The direction of the shift will depend upon the direction of change of the refractive index. Consequently, the characteristics of the interference pattern that is received at the detector 28 will vary with fluctuations in the temperature of the fluid. The output signal from the detector is received by the preamplifier 14. The operations of the preamplifier are not critical to the invention. In one embodiment, the preamplifier provides signal amplification and converts the amplified signal to a voltage output, if the output of the detector 28 is an impedance change signal. Optionally, the system 10 includes the lock-in amplifier 16. The lock-in amplifier may be used to improve the performance of operations for monitoring the phase difference between the introduction of the heat tracers and the subsequent changes in refractive index.

The interdependency between temperature and refractive index is recognized in the art. The above-cited article by H. J. Tarigan et al. describes techniques for measuring changes in refractive index. However, in most prior art references regarding optically monitoring refractive index, thermal changes are considered to be "noise." In the Tarigan et al. article, it is stated that in measuring refractive index, the primary source of interference is thermal sensitivity. However, in the system 10 of FIG. 1, the relationship between temperature and refractive index is advantageously utilized. As an alternative, the composition of the fluid may be intentionally fluctuated, since the composition will also affect the refractive index.

In operation, the heat control device 22 activates the heater 20 to introduce a heat tracer (or a repeating pattern of heat tracers) into the fluid within the passageway 12. The heat tracer will flow with the fluid toward an interrogation region defined by the laser 24 and the detector 28. When the heat tracer reaches the interrogation region, the refractive index of the fluid within the region will be perceptibly different than the refractive index of fluid that has not been heated. The output of the detector 28 will change to reflect the shift. The signal from the detector is processed using the preamplifier 14 and the lock-in amplifier 16. The processor 18 receives signals from the lock-in amplifier 16 and the heater control device 22, so that it is able to identify the transit time of the heat tracer from the heater 20 to the interrogation region. The distance that the heat tracer travels is fixed, so that the flow rate can be determined using conventional techniques.

Figure 3:
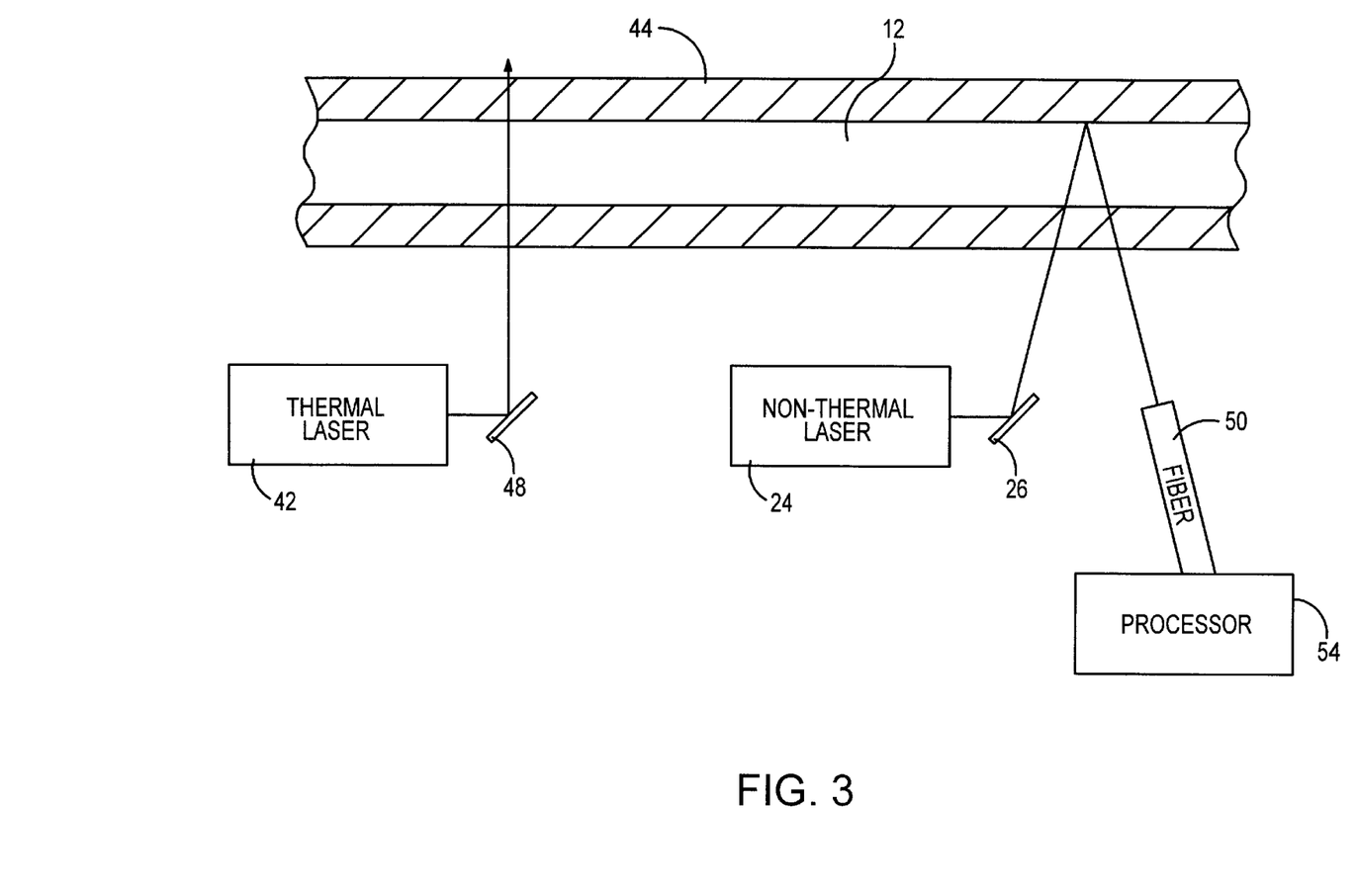
FIG. 3 is a schematic view of a second embodiment of a non-invasive fluid flow sensing system in accordance with the invention.

Another embodiment of the invention is shown in FIG. 3. In this embodiment, rather than a coil heater, a thermal laser 42 is used to introduce the heat tracer. The thermal laser may be a device that generates an infrared beam. Light within the infrared range of the light spectrum is more readily absorbed by the fluid than the light from the non-thermal laser 24 of the type described above. Other light sources, such as an infrared lamp or an LED may be substituted for the laser 42.

The embodiment of FIG. 3 utilizes a fiber 50 in place of the detector of FIG. 1. The fiber has an aperture that is dimensioned to receive as much as one maximum and one minimum or as little as one-quarter maximum or minimum from the interference pattern generated by directing the beam from the laser 24 into the interrogation region of the passageway 12. A window may be formed at the interrogation region by removing a portion of the coating 44 from the passageway, but a window is not critical. When the refractive index is changed by travel of the heat tracer into the interrogation region, the fringe maximum that is detected by the fiber will be shifted. As a result, the light intensity that propagates along the fiber will be significantly different. Other single-element arrangements may be substituted for the fiber.

The circuitry (or software capability) for calculating the transit time is represented by a processor 54. The processor receives the output from the fiber 50. While the processor is not shown as being connected to receive a signal from the thermal laser 42, the processor may be in communication with the laser. As one alternative, the processor may be made aware of a pulse of laser energy from the thermal laser 42 by an electrical connection. Alternatively, the mirror 48 may be replaced with a beam splitter that is aligned with a photodetector, not shown. A portion of the beam from the thermal laser will be directed by the beam splitter to the interrogation region of the fiber 50, while a second portion will be received by the photodetector. The photodetector may be connected to the processor 54 to provide notice that a heating pulse has been triggered. As a third alternative, the thermal laser 42 may be triggered periodically. If the periodicity is fixed and known by the processor 54, communication between the two devices is not required.

Figure 4:
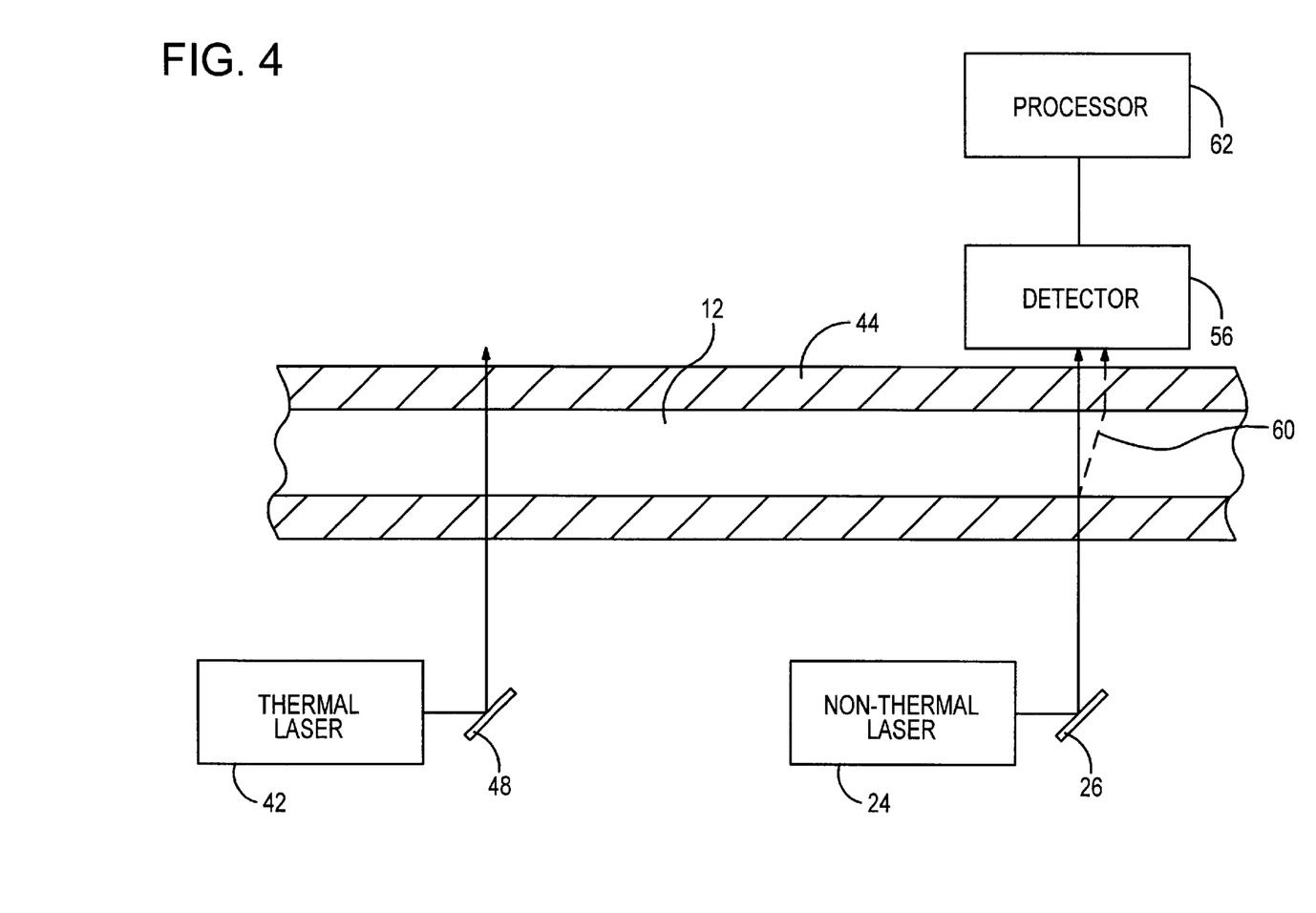
FIG. 4 is a third embodiment of a non-invasive fluid flow sensing system in accordance with the invention.

Referring now to FIG. 4, a pass-through embodiment places a detector 56 on a side of the passageway 12 opposite to the mirror 26 that reflects the laser beam from the non-thermal laser 24. Prior to heating of the fluid within the passageway by the radiation of energy from the thermal laser 42, the light from the non-thermal laser 24 will undergo a degree of refraction upon entering and exiting the passageway. Thus, the axis of the light that reaches the detector 56 will have a first angle relative to the axis of the light as it approaches the passageway. In FIG. 4, the normal state (i.e., unheated state) is indicated as a straight line from the mirror 26 to the detector 56. This is somewhat simplistic, since the light will undergo some refraction upon entering and exiting the passageway. A dashed line 60 is included in FIG. 4 to represent the change in refraction of light when the heat tracer reaches the interrogation region defined by the window 58. As can be seen, the axis of the light will strike a different portion of the detector 56. Preferably, the detector is a multi-element member, such as a CCD, but may be a single element member for position sensing. The processor 62 operates in the same manner as the processor 54 of FIG. 3 in order to determine flow rate based upon transit time of the heat tracer.

Figure 5:
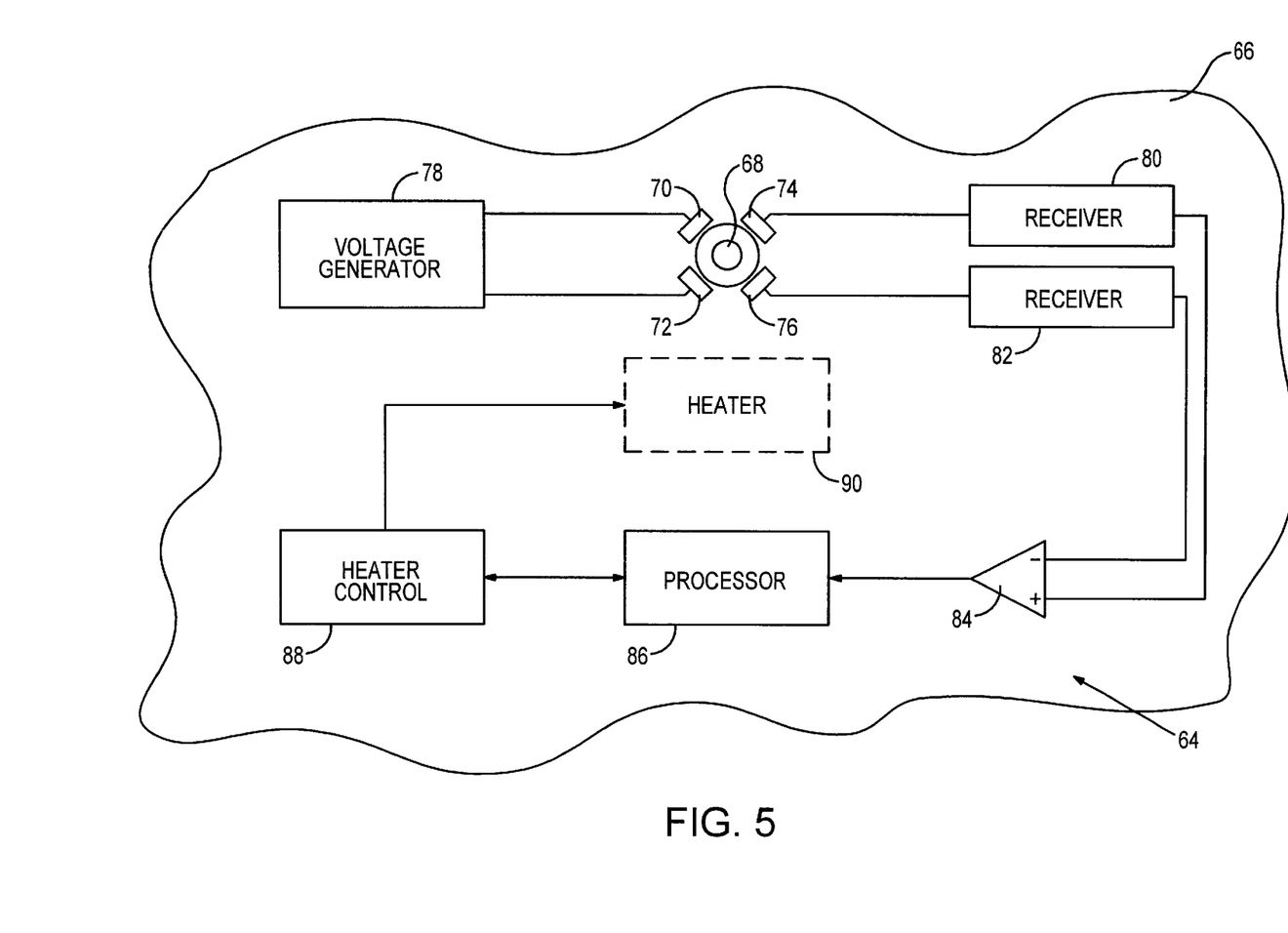
FIG. 5 is a schematic representation of a fourth embodiment of a sensing system in accordance with the invention.

Rather than monitoring the refractive index of the fluid in order to determine when a heat tracer reaches an interrogation region, the conductivity of the fluid may be monitored. An embodiment for determining flow rate based upon fluid conductivity is shown in FIG. 5. The fluid flow sensing system 64 is shown as a micro fabricated system formed on a substrate 66, such as a silicon substrate. The various components may be formed using conventional integrated circuit fabrication techniques. However, integration of the components is not desired in some applications, such as many micro analytical systems, since there are advantages to allowing the fluid-contacting components to be disposable.

The system 64 includes a flow passageway 68, such as the type used in micro analytical devices. Adjacent to the passageway are four electrodes 70, 72, 74 and 76, but other embodiments are available (e.g., a two-electrode embodiment). Conductivity detection for capillaries is presently used in the art to detect specific ionic constituents within a liquid of interest. B. Gas et al. describe an arrangement for detecting zones of ionic species that are propagating through a capillary. "High-Frequency Contactless Conductivity Detection in Isotachophoresis," *Journal of Chromatography*, 192 (1980), pages 253–257. The system of FIG. 5 is consistent with the arrangement described by B. Gas et al. However, other arrangements may be utilized without diverging from the flow rate monitoring of the present invention.

A voltage generator 78 is connected to two of the electrodes 70 and 72. The frequency of the voltage generator may be one megahertz, but this is not critical. The generator provides signals to the electrodes 70 and 72 that are 180° out of phase. The electrodes may be conductive traces on the substrate 66, while the passageway 68 may be a bore that is dimensioned to receive a conventional non-conductive capillary. Thus, at least one capacitive cell is formed. In a less complex two-electrode system, an electrical diagram would include an AC (alternating current) source connected across two capacitors that are connected in series at opposite ends of a resistor. The capacitors represent the walls of the capillary and the resistor is the fluid within the capillary.

The electrodes 74 and 76 are separately connected to receivers 80 and 82. The receivers typically include preamplification circuitry. Signals from the voltage generator are capacitively coupled through the passageway 68 and are detected by the receivers 80 and 82. The outputs from the receivers are responsive to the strengths of the signals received at the electrodes 74 and 76. In the application illustrated in FIG. 5, the output signals from the receivers are connected to a differential amplifier 84. The signal from the differential amplifier is responsive to the difference between the strengths of signals from the receivers, since the inputs to the electrodes 70 and 72 are 180° out of phase. However, use of a differential amplifier is not critical to the invention. Rather than coupling the receivers to a differential amplifier, the outputs from the receivers may be connected to an adder that may provide additional sensitivity to fluctuations in the conductivity of fluid within the passageway 68.

The differential amplifier 84 is connected to a processor 86, which is also in communication with a heater control device 88. The heater control device is used to activate and deactivate a heater that is in thermal communication with the passageway 68. Since the heater is preferably (but not necessarily) located at a position along the passageway that is different than the interrogation region defined by the positions of the electrodes 70–76, the heater is shown in phantom. Optionally, the heater may be on one side of the substrate 66, while the electrodes are on the opposite side of the substrate.

Prior to activation of the heater 90, the fluid within the passageway 68 will have a particular level of conductivity. The conductivity will be dependent upon the ionic species that are constituent to the fluid of interest and upon any electrolyte that is used. If the flow rate sensing is performed early within the process of separating the various species using capillary electrophoresis techniques, the conductivity will be sufficiently constant. On the other hand, if a significant amount of species separation has occurred prior to the flow rate monitoring, the processor 86 is preferably configured to compensate for the fluctuations in fluid conductivity as a result of species separation. In a non-complex application, the heater control device 88 may provide a notification signal to the processor 86 that the heater 90 has been activated to introduce a heat tracer, so that the processor is able to anticipate the arrival of the heat tracer at the interrogation region defined by the electrodes 70–76. This notification technique enables the processing circuitry to distinguish species-dependent conductivity fluctuations from the anticipated thermal-dependent conductivity fluctuation. More complex techniques may be substituted.

Figure 7:
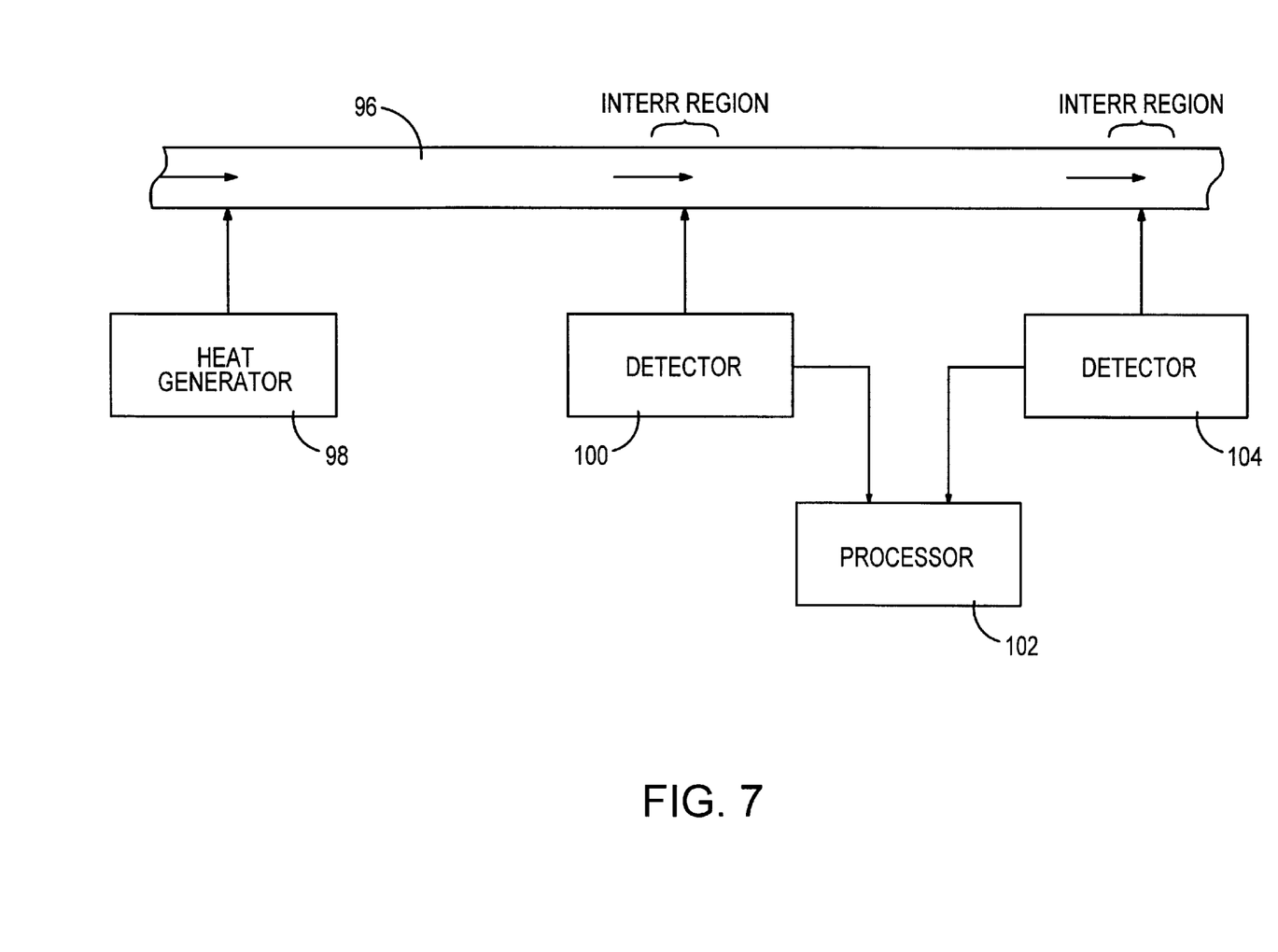
FIG. 7 is a schematic view of a second application of the systems of FIGS. 1 and 3–5.

As an alternative to the cross-channel capacitively coupled embodiment of FIG. 5, conductivity fluctuations within the passageway 68 may be determined by capacitively coupling electrodes along the length of the passageway. Referring briefly to FIG. 7, the electrodes may be rings that are positioned at the interrogation regions of the two detectors 100 and 104. However, rather than two interrogation regions, there would be a single interrogation region along the lengthwise portion of the passageway between the two ring-shaped electrodes. When a heat tracer reaches the lengthwise interrogation region, the conductivity within this region will increase. Using the signaling techniques described with reference to FIG. 5, the detection of the heat tracer within the interrogation region may be used to determine the flow rate within the passageway.

Figure 6:
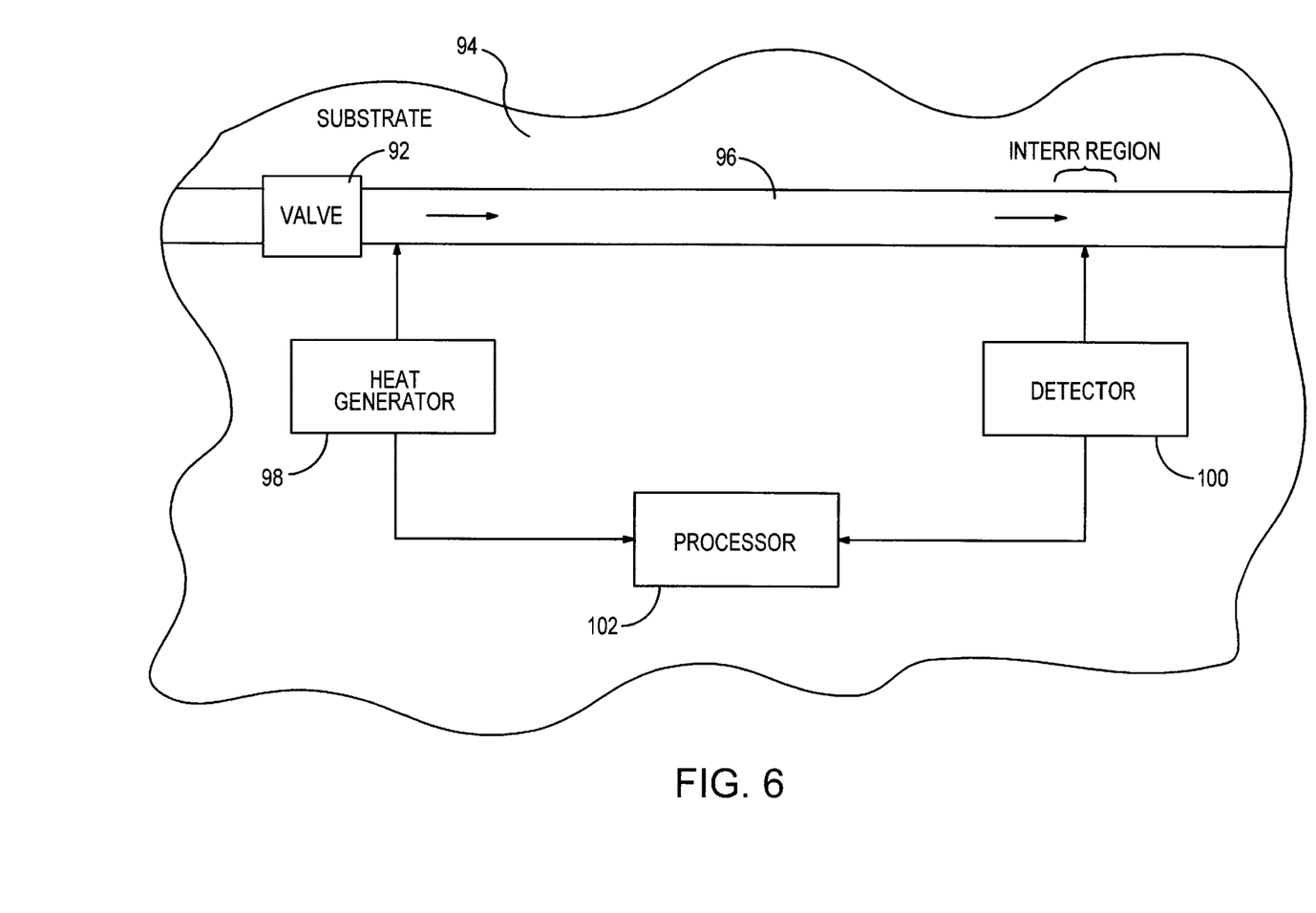
FIG. 6 is a view of one application of the sensing systems of FIGS. 1 and 3–5.

Various applications of the systems of FIGS. 1 and 3–5 are shown in FIGS. 6–9. Within the different applications, the equivalent components are assigned the same reference numerals. In FIG. 6, a micro machined valve 92 is fabricated on a substrate 94, such as a silicon substrate. A channel 96 is formed within the substrate for conducting fluid. Alternatively, one or more capillary tubes may be fixed to the surface of the substrate. While not shown in FIG. 6, a pumping mechanism may also be included on the surface of the substrate.

After fluid has passed through the micro machined valve 92, a heat generator 98 is used to selectively introduce heat tracers. A heat tracer will propagate through the passageway to an interrogation region defined by the position of a detector 100. The detector may be any one of the optical or electrical arrangements described with reference to FIGS. 1–5. When the physical properties of the fluid within the interrogation region are changed as a result of the thermal energy introduced by the heat tracer, the detector will sense the change in physical properties. For example, if the detector is used to sense changes in refractive index, the fluctuations in received optical energy as a result of the heat tracer will be sensed by the detector. The output signal from the detector is utilized by a processor 102 to determine the flow rate over the distance from the position of the heat generator 98 to the interrogation region.

Turning now to FIG. 7, a second detector 104 may be used to monitor flow rate between two interrogation regions, rather than monitoring flow rate from the position of the heat generator 98 to the first interrogation region defined by the detector 100. The first detector 100 will sense the arrival of the heat tracer at a region that is downstream of the heat generator, but upstream of the interrogation region of the second detector. The heat tracer will pass through the first interrogation region and will subsequently be detected by the second detector. The time necessary for propagation of the heat tracer between the two interrogation regions may be used to calculate the flow rate over the fixed distance between the two interrogation regions. For a fixed modulation of the heat generator 98, the phase difference between the two detections may be used to determine the flow rate.

Figure 8:
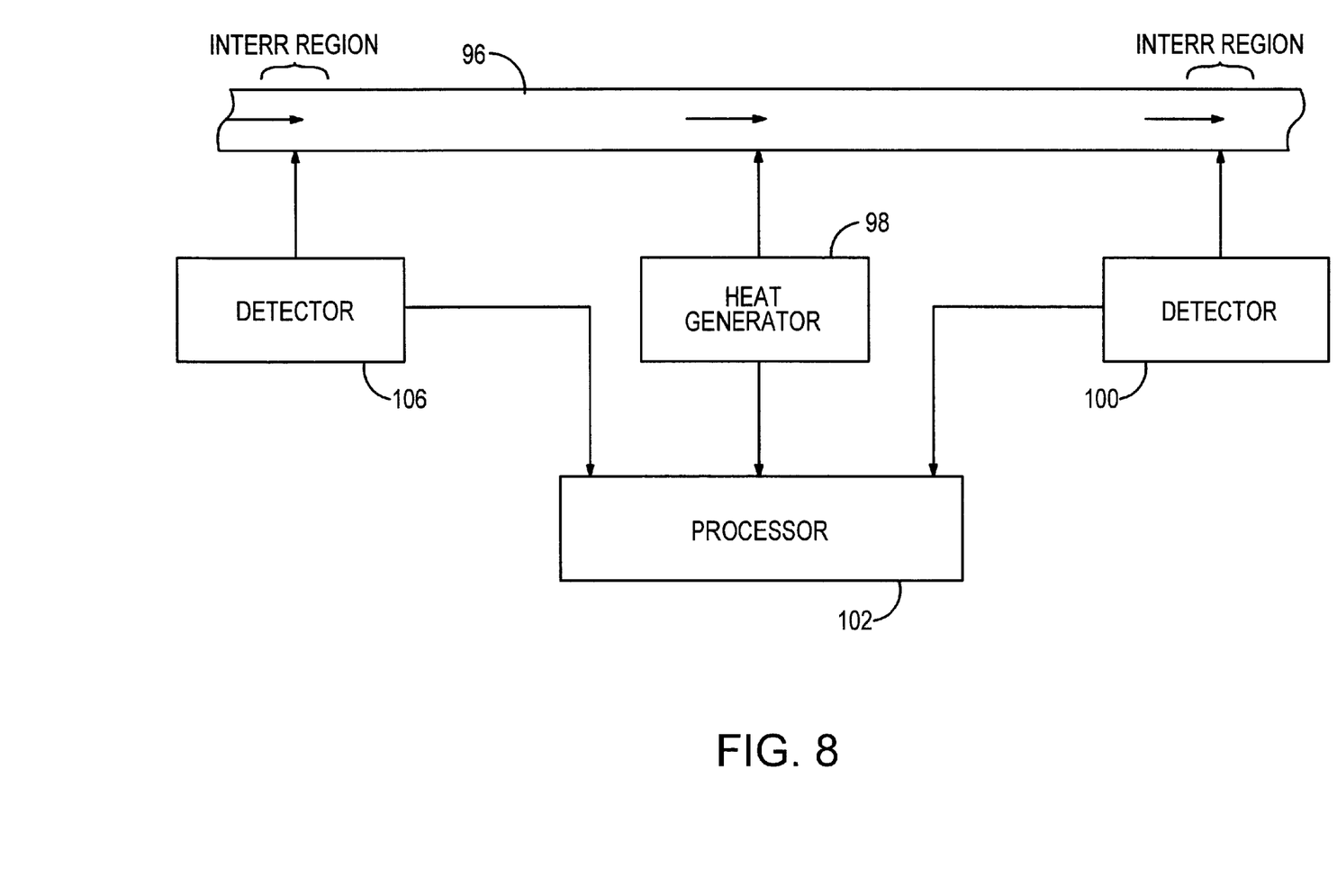
FIG. 8 is a schematic view of a third application of the systems of FIGS. 1 and 3–5.

FIG. 8 illustrates an application in which the thermal dilution approach to sensing flow rate may be utilized. According to the thermal dilution principle, the flow rate is determined based upon monitoring techniques that are implemented both upstream and downstream of a heat generator 98. The operations of the heat generator 98 and the detector 100 are similar to those described with reference to FIG. 6. However, an upstream detector 106 is positioned to sense the refractive index or conductivity at the upstream interrogation region. The interrogation regions of the detectors 100 and 106 are equidistant from the heat generator.

When a heat tracer is introduced by the heat generator 98, thermal energy will flow both upstream and downstream. The flow rate of the upstream radiation will depend upon the rate of the counterflow of fluid within the passageway 96. The processor 102 is configured to calculate fluid flow rate based upon the detection of fluctuations in the physical properties of fluid that are experienced within the two interrogation regions.

Figure 9:
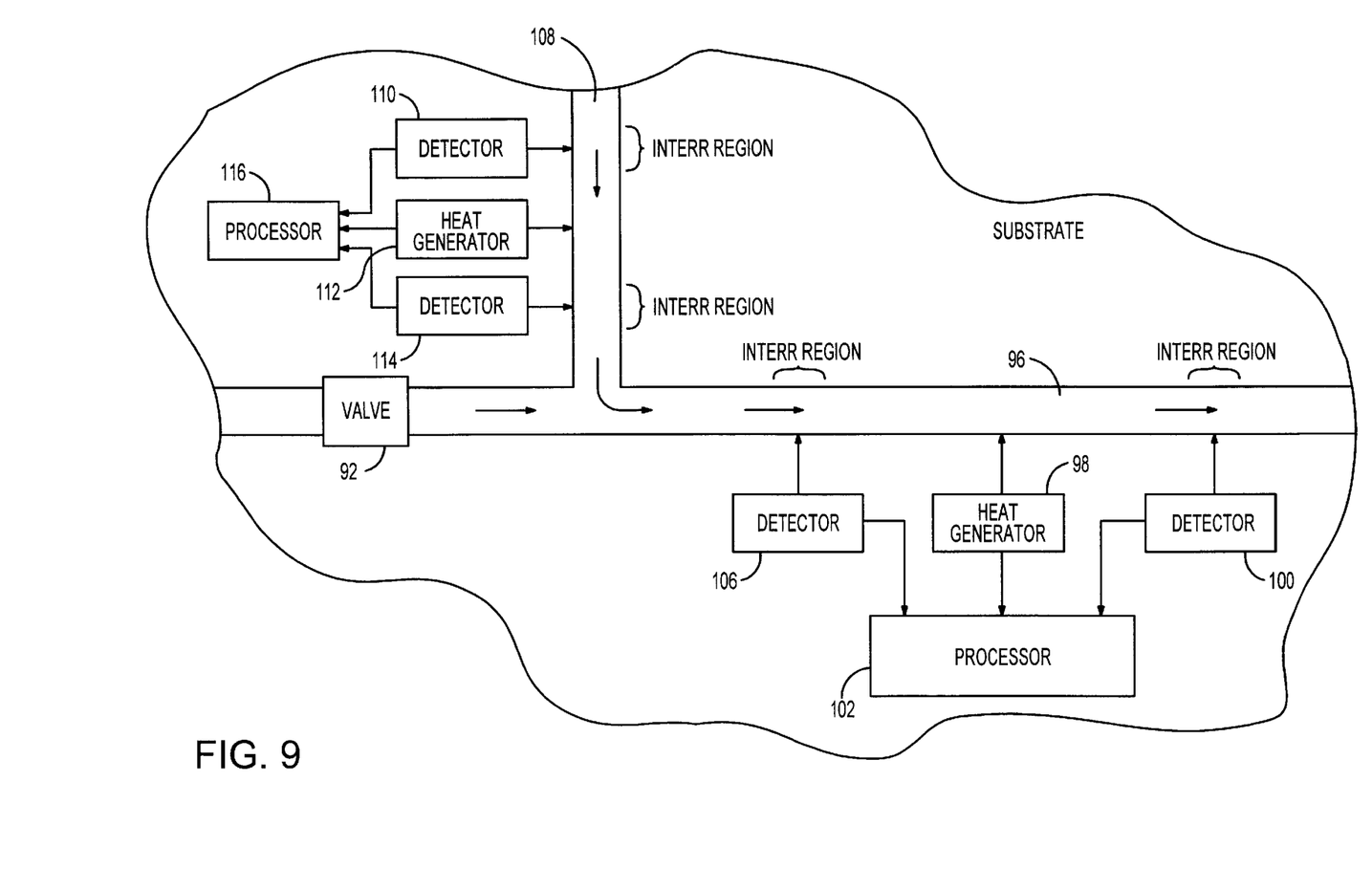
FIG. 9 is a schematic top view of a fourth application of the systems of FIGS. 1 and 3–5.

In FIG. 9, a feed path 108 has been added to the passageway 96 described with reference to FIG. 8. In practice, the micro machined valve 92 may be used to regulate flow of an electrolyte, while a solution of interest is introduced along the feed path 108. The system that includes the heat generator 98, the two detectors 100 and 106, and the processor 102 is duplicated along the length of the feed path 108. The "redundant" system includes a detector 110 that is upstream from a heat generator 112 and includes a detector 114 that is downstream of the heat generator. The signals from the detectors are manipulated by a processor 116 to determine the flow rate along the feed path.

By monitoring the refractive index or the conductivity (i.e., the resistivity) of the fluid in order to determine flow rate, the necessary data can be obtained without direct contact between the monitoring equipment and the fluid of interest. Consequently, the monitoring process does not introduce contamination into the stream. Moreover, fluid temperature is monitored indirectly, so that substrate temperature is not a factor and there is no need to compensate for any thermal conductivity from a heat generator to a heat sensor. Likewise, there is no heat transfer from the fluid to the detector. Unlike temperature sensors of the prior art, sensitivity is not affected by the size of the sensors. As noted above, the flow rate determination may also be used in a feedback control of the heater, thereby regulating the temperature along the flow path without significantly increasing the required circuitry.

What is claimed is:

1. A system for monitoring flow comprising:
   a fluid-bearing passageway having an interrogation region;
   a heat generator that is physically isolated from fluid flow through said fluid-bearing passageway while being in thermal transfer engagement with said fluid-bearing passageway, said heat generator being configured to selectively introduce temperature fluctuations into said fluid flow through said fluid-bearing passageway;
   one of an optical and electrical source that is physically isolated from said fluid flow through said fluid-bearing passageway while being operationally associated with said interrogation region to form at least one of a capacitive cell and a light probing arrangement at said interrogation region;
   a detector positioned relative to said interrogation region to monitor temperature changes within said interrogation region, said detector being configured to measure at least one of resistivity within said interrogation region and light redirected at said interrogation region as a result of interaction with said fluid flow and said fluid-bearing passageway; and
   rate determination capability connected to said detector to monitor progress of said temperature fluctuations through said fluid-bearing passageway on a basis of measurements of at least one of resistivity and refractive index, said rate determination capability being configured to identify fluid flow rate within said fluid-bearing passageway based upon said monitoring of said progress.

2. The system of claim 1 wherein said source includes a laser and wherein said detector is positioned to detect an interference pattern generated by redirections of incident light from said fluid flow and said fluid-bearing passageway.

3. The system of claim 2 wherein said detector is an imaging detector having a field of view that is sufficiently large to detect a plurality of maxima of said interference pattern.

4. The system of claim 2 wherein said detector is a single-element light sensor having a field of view that is restricted to detecting less than two adjacent maxima or two adjacent minima of said interference pattern.

5. The system of claim 2 wherein said laser has a center wavelength of less than 1100 nm and wherein said heat generator is a heating laser having a center wavelength within the infrared range of the light spectrum.

6. The system of claim 2 wherein said laser and said detector are cooperative to propagate light energy through said fluid-bearing passageway and to detect said light energy, said rate determination capability being adapted to identify temperature fluctuations within said fluid-bearing passageway based upon angular fluctuations of the axis of said light energy following propagation through said fluid flow and said fluid-bearing passageway.

7. The system of claim 1 wherein said source is configured to form a capacitive cell by positioning electrode plates adjacent to said fluid-bearing passageway and wherein said detector measures resistivity of fluid within said interrogation region.

8. The system of claim 1 wherein said fluid-bearing passageway is a capillary tube micro.

9. The system of claim 1 further comprising:
   a second source of optical or electrical energy physically isolated from but operationally associated with said fluid flow upstream of said heat generator, thereby defining a second interrogation region; and
   a second detector positioned relative to said second interrogation region of said fluid-bearing passageway to monitor temperature changes within said interrogation region, said detector being configured to measure at least one of resistivity and light redirected at said second interrogation region, said second detector having an output that is indicative of measurements of said at least one of said resistivity and said redirected light;
   wherein said rate determination capability is enabled to dynamically identify said flow rate based upon temperature-dependent differences in at least one of resistivities and refractive indices upstream and downstream of said heat generator.

10. A method of monitoring flow in a fluid-bearing passageway comprising steps of:
- introducing propagating heat fluctuations into a flow of liquid through said passageway, said propagating heat fluctuations being introduced at a first position along said passageway;
- measuring temperature-dependent changes in resistivity of said liquid along a first interrogation region of said passageway, including monitoring said resistivity over a period of time sufficiently great to enable at least one said propagating heat fluctuation to propagate into said first interrogation region; and
- determining a flow rate of said liquid based upon said monitoring of said resistivity to determine times for said propagating heat fluctuations to travel from said first position to said interrogation region.

11. The method of claim 10 wherein said step of measuring resistivity includes applying an alternating current to electrodes positioned adjacent to said first interrogation region and includes calculating measurements of resistivity on a basis of parameters related to capacitive coupling across said electrodes.

12. The method of claim 10 further comprising steps of:
- measuring temperature-dependent changes in resistivity of said liquid along a second interrogation region of said passageway, said first and second interrogation regions being on opposite sides of said first position, including monitoring said resistivity along said second interrogation region over said period of time simultaneously with monitoring said resistivity along said first interrogation region; and
- utilizing said step of monitoring said resistivity along said second interrogation region to determine said flow rate.

13. The method of claim 12 wherein said steps of introducing said propagating heat fluctuations and measuring resistivity are implemented in an absence of physical contact between said liquid and equipment for performing said steps, said step of determining said flow rate including monitoring shifts between a phase of said heat fluctuations and a phase of fluctuations in resistivity.

14. The method of claim 10 further comprising providing a capillary having a cross sectional dimension of less than 500 $\mu$m and includes directing a liquid of interest through said capillary, thereby providing said fluid-bearing passageway.

15. A method of monitoring flow in a fluid-bearing passageway comprising steps of:
- introducing heat fluctuations into a flow of liquid through said passageway, said heat fluctuations being introduced at a first position along said passageway;
- directing a beam from a light source into said liquid at a first interrogation region of said passageway;
- detecting light energy from said beam following interaction of said light energy with said liquid, including monitoring refractive index of said liquid over a period of time; and
- determining a flow rate of said liquid based upon said monitoring of said refraction index and upon determining times required for said heat fluctuations to travel from said first position to said first interrogation region, including detecting entrances of said heat fluctuations into said first interrogation region by correlating changes in said refractive index with said entrances of said heat fluctuations.

16. The method of claim 15 wherein said step of monitoring said refraction index includes detecting an interference pattern created by said step of directing said beam, and wherein said step of determining said flow rate includes determining calculations of said flow rate on a basis of variations in said interference pattern as a function of said entrances of said heat fluctuations into said first interrogation region.

17. The method of claim 15 further comprising steps of:
- directing a second beam into said liquid at a second interrogation region that is upstream of said first position and said first interrogation region;
- detecting light energy from said second beam following refraction as a result of interaction with said liquid; and
- utilizing said detected light from said second beam in said step of determining said flow rate.

18. The method of claim 15 wherein said step of detecting said light energy includes determining fluctuations in angles of said light energy that propagates through said liquid.

19. The method of claim 15 wherein said step of introducing said heat fluctuations includes directing modulated infrared light into a capillary and wherein said step of directing said beam includes utilizing a laser source having a center frequency that does not exceed 1100 nm.

* * * * *